US00PP18970P2

(12) United States Plant Patent
Hooijman

(10) Patent No.: US PP18,970 P2
(45) Date of Patent: Jun. 24, 2008

(54) ***LIMONIUM* PLANT NAMED 'ESM ARROZ'**

(50) Latin Name: *Limonium sinense*
Varietal Denomination: Esm Arroz

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 2 days.

(21) Appl. No.: 11/489,198

(22) Filed: Jul. 19, 2006

(51) Int. Cl.
*A01H 5/00* (2006.01)

(52) U.S. Cl. ..... Plt./358

(58) Field of Classification Search ..... Plt./358
See application file for complete search history.

(56) References Cited

PUBLICATIONS

Upovrom PBR 20041701 Plant Variety Database, p. 1.*

* cited by examiner

*Primary Examiner*—Annette H Para
(74) *Attorney, Agent, or Firm*—C. A. Whealy

(57) ABSTRACT

A new and distinct cultivar of *Limonium* plant named 'Esm Arroz', characterized by its erect, long and strong flowering stems; vigorous growth habit; freely flowering habit; small white-colored flowers that do not fully open; and good postproduction longevity.

1 Drawing Sheet

Botanical designation: *Limonium sinense.*
Cultivar denomination: 'Esm Arroz'.

BACKGROUND OF THE INVENTION

The present invention relates to a new and distinct cultivar of *Limonium* plant, botanically known as *Limonium sinense,* grown commercially as a cut flower, and hereinafter referred to by the name 'Esm Arroz'.

The new *Limonium* is a product of a planned breeding program conducted by the Inventor in El Quinche, Pichincha, Ecuador. The objective of the breeding program is to create new freely flowering *Limonium* cultivars with long and straight flowering stems.

The new *Limonium* originated from a open-pollination in El Quinche, Pichincha, Ecuador in February, 2000 of a proprietary selection of *Limonium sinense* identified as Line 57, not patented, as the female, or seed, parent with an unknown selection of *Limonium sinense.* The cultivar Esm Arroz was discovered and selected by the Inventor as a flowering plant from within the progeny of the stated open-pollination in a controlled environment in El Quinche, Pichincha, Ecuador.

Asexual reproduction of the new *Limonium* by cuttings in a controlled environment in El Quinche, Pichincha, Ecuador since February, 2001, has shown that the unique features of this new *Limonium* are stable and reproduced true to type in successive generations.

SUMMARY OF THE INVENTION

The cultivar Esm Arroz has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Esm Arroz'. These characteristics in combination distinguish 'Esm Arroz' as a new and distinct cultivar of *Limonium:*

1. Erect, long and strong flowering stems.
2. Vigorous growth habit.
3. Freely flowering habit.
4. Small white-colored flowers that do not fully open.
5. Good postproduction longevity.

In side-by-side comparisons conducted in El Quinche, Pichincha, Ecuador, plants of the new *Limonium* differed from plants of the female parent selection in the following characteristics:

1. Plants of the new *Limonium* were more freely flowering than plants of the female parent selection.
2. Flowers of the new *Limonium* did not fully open whereas flowers of plants of the female parent selection opened.

Plants of the new *Limonium* can be compared to plants of the *Limonium* cultivar China White, not patented. In side-by-side comparisons conducted in El Quinche, Pichincha, Ecuador, plants of the new *Limonium* differed from plants of the cultivar China White in the following characteristics:

1. Plants of the new *Limonium* were more vigorous and had stronger flowering stems than plants of the cultivar China White.
2. Plants of the new *Limonium* had longer leaves than plants of the cultivar China White.
3. Plants of the new *Limonium* were more freely flowering than plants of the cultivar China White.
4. Flowers of the new *Limonium* did not fully open whereas flowers of plants of the cultivar China White opened.
5. Plants of the new *Limonium* had longer postproduction longevity than plants of the cultivar China White.

BRIEF DESCRIPTION OF THE PHOTOGRAPHS

The accompanying photographs illustrate the overall appearance of the new *Limonium.* The photographs show the colors as true as it is reasonably possible to obtain in colored reproductions of this type. Colors in the photographs may differ slightly from the color values cited in the detailed botanical description which accurately describe the colors of the new *Limonium*. Clockwise from the upper left photograph: side perspective view of a typical flowering stem; close-up of a typical inflorescence; close-up view of upper and lower surfaces of typical leaves; and close-up view of a typical flowering stem of 'Esm Arroz'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown during the winter in El Quinche, Pichincha, Ecuador in ground beds in a polyethylene-covered greenhouse and under conditions and practices which approximate those generally used in commercial cut *Limonium* production. During the production of the plants, day temperatures ranged from 11° C. to 28° C., night temperatures ranged from 5° C. to 11° C. and light levels ranged from 1,000 to 1,150 foot-candles. Plants were pinched. Measurements and numerical values represent averages for typical five-month old flowering plants.

Botanical classification: *Limonium sinense* cultivar Esm Arroz.

Commercial classification: Cut flower *Limonium*.

Parentage:

*Female, or seed, parent.*—Proprietary selection of *Limonium sinense* identified as Line 57, not patented.

*Male, or pollen, parent.*—Unknown selection of *Limonium sinense,* not patented.

Propagation:

*Type.*—By cuttings.

*Time to initiate roots.*—About 15 to 20 days at 17° C. to 25° C.

*Time to produce a rooted cutting.*—About seven to nine weeks at 17° C. to 25° C.

*Root description.*—Fine; 161B in color.

Plant description:

*Appearance.*—Perennial subshrub grown as a cut flower. Erect and strong flowering stems; inverted triangle form. Leaves basal. Freely flowering habit; numerous flowers arranged in symmetrical and moderately dense compound panicles. Vigorous growth habit.

*Branching habit.*—After pinching, about 32 flowering stems develop per year.

*Plant height.*—About 119 cm.

*Plant diameter or spread.*—About 99 cm.

*Flowering stems.*—Length: About 119 cm. Diameter: About 7 mm. Internode length: About 5.5 cm. Strength: Strong. Texture: Immature, pubescent; mature, glabrescent. Color: 147A.

Foliage description:

*Arrangement.*—Alternate, simple; sessile.

*Length.*—About 35 cm.

*Width.*—About 5.4 cm.

*Shape.*—Narrowly obovate.

*Apex.*—Obtuse.

*Base.*—Attenuate.

*Margin.*—Crenate; undulate.

*Texture, upper and lower surfaces.*—Smooth, glabrous; waxy.

*Venation pattern.*—Pinnate.

*Color.*—Developing foliage, upper surface: 146A. Developing foliage, lower surface: 147B. Fully expanded foliage, upper surface: 147A to 137A; venation, 157A. Fully expanded foliage, lower surface: 137B; venation, 145C.

Flower description:

*Flower arrangement and habit.*—Compound cymes with numerous flowers; flowers actinomorphic and symmetrical. Very freely flowering, about 8,700 flowers per inflorescence. Flowers face mostly upright.

*Flowering response.*—In Ecuador, plants flower year round. Plants begin flowering about 16 weeks after planting.

*Post-production longevity.*—As a cut flower, flowers last for about two weeks.

*Fragrance.*—None detected.

*Inflorescence height.*—About 119 cm.

*Inflorescence diameter.*—About 72 cm.

*Flower diameter.*—About 6 mm.

*Flower depth (height).*—About 7 mm.

*Flower buds.*—Length: About 7 mm. Diameter: About 2 mm. Shape: Fusiform. Color: Towards the apex, close to 155D; towards the base, 144A.

*Corolla.*—Petals per flower: About four to eight. Petal length: About 6 mm. Petal width: About 2 mm. Petal shape: Irregular. Petal apex: Emarginate. Petal margin: Entire. Petal texture, upper and lower surfaces: Smooth, glabrous; membraneous. Petal color: When opening, upper and lower surfaces: Close to 155D; towards the base, close to 145B. Fully opened, upper and lower surfaces: Close to 155D; towards the base, close to 160C.

*Calyx.*—Sepals per flower: Five. Length: About 5 mm. Width: About 6 mm. Shape: Salverform. Sepal apex: Acute. Sepal margin: Entire. Sepal texture, upper and lower surfaces: Smooth, glabrous. Sepal color: When opening, upper surface: Close to 155D; throat, 146C. When opening, lower surface: Close to 155D; tube, 144B. Fully opened, upper surface: Close to 155D; throat, 144C. Fully opened, lower surface: Close to 155D; tube, N144D.

*Pedicels.*—Length: About 13.6 cm. Diameter: About 7 mm. Strength: Strong. Angle: About 56° from vertical. Texture: Smooth, glabrous. Color: 147A.

*Reproductive organs.*—None observed.

*Seeds.*—None observed.

Disease/pest resistance: Plants of the new *Limonium* have been observed to be resistant to *Peronospora*. Plants have not been shown to be resistant to pests and other pathogens common to *Limonium*.

Temperature tolerance: Plants of the new *Limonium* have been observed to tolerate temperatures ranging from about 5° C. to about 30° C.

It is claimed:

1. A new and distinct *Limonium* plant named 'Esm Arroz' as illustrated and described.

* * * * *

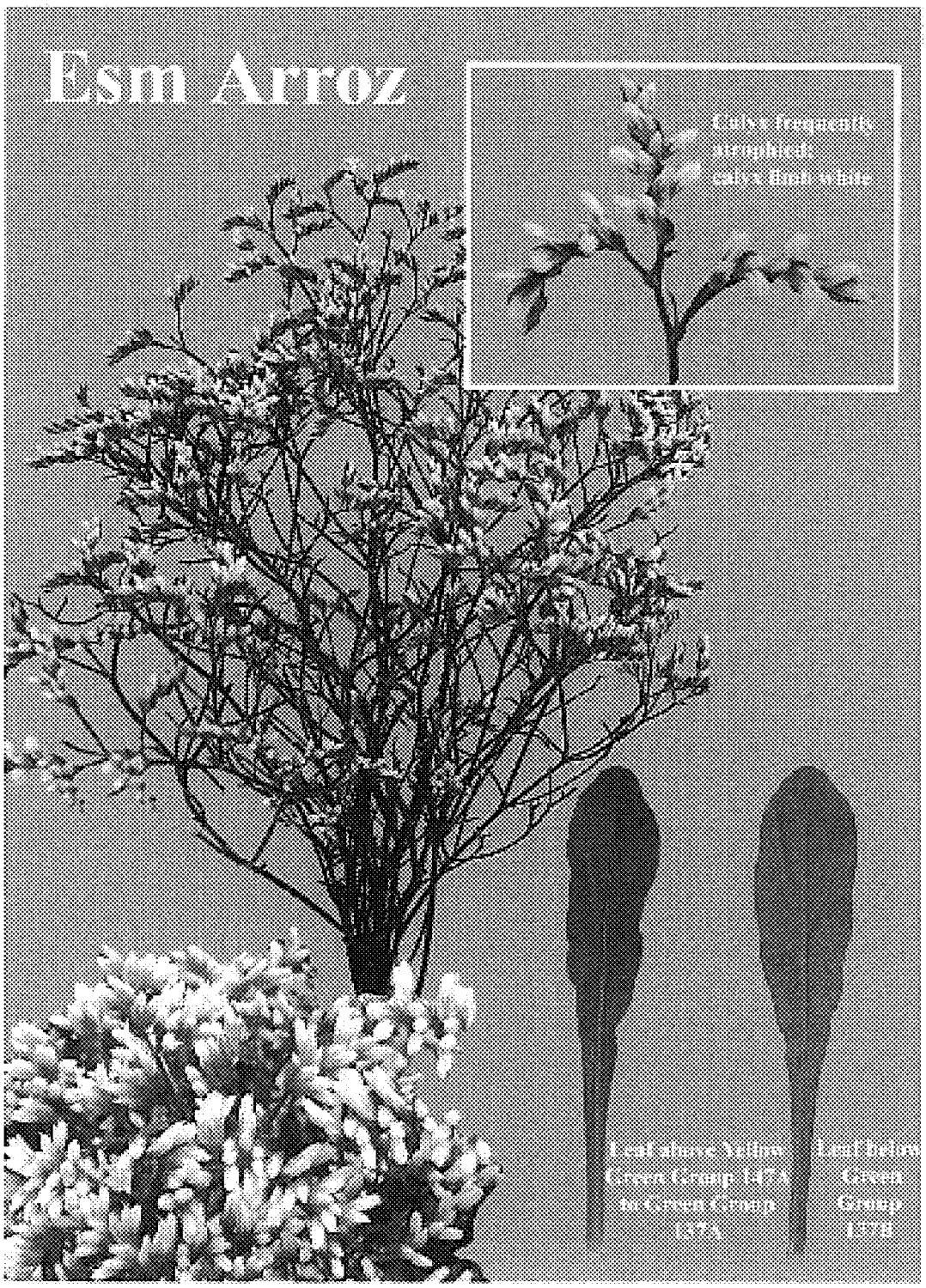
Esm Arroz
Calyx fragrantly
scented
calyx light white
Leaf above Yellow
Green Group 147A
to Green Group
137A
Leaf below
Green
Group
137B